US011754520B2

(12) United States Patent
Sun et al.

(10) Patent No.: US 11,754,520 B2
(45) Date of Patent: Sep. 12, 2023

(54) DYNAMIC IMPEDANCE IMAGING SYSTEM

(71) Applicant: Beihang University, Beijing (CN)

(72) Inventors: Jiangtao Sun, Beijing (CN); Xu Bai, Beijing (CN); Lijun Xu, Beijing (CN); Wenbin Tian, Beijing (CN); Yuedong Xie, Beijing (CN)

(73) Assignee: BEIHANG UNIVERSITY, Beijing (CN)

( * ) Notice: Subject to any disclaimer, the term of this patent is extended or adjusted under 35 U.S.C. 154(b) by 147 days.

(21) Appl. No.: 17/458,065

(22) Filed: Aug. 26, 2021

(65) Prior Publication Data

US 2023/0082500 A1 Mar. 16, 2023

(51) Int. Cl.
*G01N 27/06* (2006.01)
*A61B 5/0536* (2021.01)
*A61B 5/0265* (2006.01)

(52) U.S. Cl.
CPC ........... *G01N 27/06* (2013.01); *A61B 5/0536* (2013.01); *A61B 5/0265* (2013.01)

(58) Field of Classification Search
CPC ........ G01N 29/02; G01N 27/02; G01N 27/06; G01N 27/12; G01N 27/026;
(Continued)

(56) References Cited

U.S. PATENT DOCUMENTS 6,387,671 B1 * 5/2002 Rubinsky ......... G01N 33/48728 435/173.7
6,940,286 B2 * 9/2005 Wang ..................... G01N 27/24 324/603
(Continued)

FOREIGN PATENT DOCUMENTS

CN 108037156 A * 5/2018
CN 111543993 A * 8/2020 ........... A61B 5/0536
(Continued)

OTHER PUBLICATIONS

Bai et al., Electrical Impedance Tomography System Based on Time Interleaved Analog to Digital Converter. IEEE 2022. (Year: 2022).*
(Continued)

*Primary Examiner* — Jermele M Hollington
*Assistant Examiner* — Sean Curtis
(74) *Attorney, Agent, or Firm* — Lucas & Mercanti,LLP

(57) ABSTRACT

A dynamic impedance imaging system includes a dynamic impedance imaging sensor, an impedance detection and flow rate measurement module and an electrical impedance tomography (EIT) instrument. The impedance detection and flow rate measurement module is configured to detect an abnormal particle flowing through the dynamic impedance imaging sensor to obtain a flow rate of the abnormal particle, and generate a synchronous trigger signal. The EIT instrument is configured to inject a sinusoidal excitation current into the dynamic impedance imaging sensor under the trigger of the synchronous trigger signal, perform multi-channel interleaved sampling for the abnormal particle according to the flow rate to acquire multi-channel sampled data, and calibrate the multi-channel sampled data to implement impedance tomography imaging for the abnormal particle.

7 Claims, 6 Drawing Sheets

(58) Field of Classification Search
CPC .......... G01N 2015/1445; A61B 5/0536; A61B 5/063; A61B 5/0265; A61B 5/0033
USPC .............................. 324/693; 73/53.01, 53.04
See application file for complete search history.

(56) References Cited

U.S. PATENT DOCUMENTS

| | | | | |
|---|---|---|---|---|
| 9,909,910 | B2 * | 3/2018 | Kersey | G01F 1/712 |
| 10,732,017 | B2 * | 8/2020 | Wang | G01F 1/7088 |
| 10,781,687 | B2 * | 9/2020 | Huang | G01F 1/64 |
| 11,293,279 | B1 * | 4/2022 | Karra | E21B 43/26 |
| 2012/0232810 | A1 * | 9/2012 | Kaipio | G01N 27/06 702/45 |
| 2015/0253164 | A1 * | 9/2015 | Kersey | G01F 1/704 73/861.08 |
| 2017/0261357 | A1 * | 9/2017 | Wang | G01F 1/74 |
| 2018/0347341 | A1 * | 12/2018 | Huang | G01V 3/20 |
| 2023/0082500 | A1 * | 3/2023 | Sun | G01N 27/06 324/693 |

FOREIGN PATENT DOCUMENTS

| | | | | |
|---|---|---|---|---|
| CN | 111938642 | A * | 11/2020 | |
| CN | 113098512 | A * | 7/2021 | G01R 27/02 |
| CN | 111543993 | B * | 1/2022 | A61B 5/0536 |
| CN | 115670420 | A * | 2/2023 | |
| EP | 3649934 | B1 * | 12/2020 | A61B 5/0536 |
| WO | WO-2016042317 | A1 * | 3/2016 | G01F 1/58 |

OTHER PUBLICATIONS

B Murat Eyüboglu, An interleaved drive electrical impedance tomography image reconstruction algorithm. 1996 Physiol. Meas. 17 A59 (Year: 1996).*

Yao et al., Application of Process Tomography to Multiphase Flow Measurement in Industrial and Biomedical Fields: A Review. IEEE Sensors Journal, vol. 17, No. 24, Dec. 15, 2017 (Year: 2017).*

Wi et al., Multi-Frequency Electrical Impedance Tomography System With Automatic Self-Calibration for Long-Term Monitoring. IEEE Transactions on Biomedical Circuits and Systems, vol. 8, No. 1, Feb. 2014 (Year: 2014).*

Hu et al., An impedance-analyser-based multi-channel imaging system and its applications. IEEE International Workshop on Imaging Systems and Techniques—IST 2008 (Year: 2008).*

English Translation of CN-111543993 A. (Year: 2020).*

Texas Instruments. TI Designs: TIDA-01355 Analog Front-End Reference Design for Imaging Using Time-Interleaved SAR ADCs With 73-dB SNR, 7.5 MSPS. Aug. 2017 (Year: 2017).*

* cited by examiner

DYNAMIC IMPEDANCE IMAGING SYSTEM

TECHNICAL FIELD

The present disclosure relates to the field of Electrical Impedance Tomography (EIT), and in particular to a dynamic impedance imaging system.

BACKGROUND ART

As a low-cost, non-invasive and radiation-free imaging technology, electrical impedance tomography (EIT) has been widely used in industrial process imaging and medical imaging. Imaging abnormal particles in the fluid has a bright prospect in medical science. As an example, imaging cancer cell clusters in the blood may be useful in determining the incidence of early-stage cancer and whether the cancer has metastasized. For similar reasons, whether there is an embolism in the blood vessel can be determined by imaging abnormal particles in the blood. Multiphase flow detection may likewise be promoted by imaging abnormal particles in the fluid, for example, to detect bubbles in liquid.

At present, the existing EIT equipment lacks the ability to image abnormal particles in the fluid. Moreover, in practical applications of the biomedical field, the EIT system is required to increase the sampling rate (bandwidth) as much as possible while ensuring the signal-to-noise ratio (SNR).

SUMMARY

In view of this, it is necessary to provide a dynamic impedance imaging system to realize the imaging of an abnormal particle in a fluid while meeting the requirements for bandwidth and the SNR in the fields of biomedicine and multiphase flow.

In order to achieve the above object, the present disclosure provides the following solution.

A dynamic impedance imaging system includes a dynamic impedance imaging sensor, an impedance detection and flow rate measurement module and an electrical impedance tomographic (EIT) instrument, where

- the dynamic impedance imaging sensor is connected to the impedance detection and flow rate measurement module; the dynamic impedance imaging sensor is configured to determine whether there is an abnormal particle flowing through a tube;
- the impedance detection and flow rate measurement module is configured to detect the abnormal particle flowing through the dynamic impedance imaging sensor to obtain a flow rate of the abnormal particle, and generate a synchronous trigger signal;
- the EIT instrument is respectively connected to the impedance detection and flow rate measurement module and the dynamic impedance imaging sensor; the EIT instrument is configured to inject a sinusoidal excitation current into the dynamic impedance imaging sensor under triggering of the synchronous trigger signal, to perform multi-channel interleaved sampling for the abnormal particle according to the flow rate to acquire multi-channel sampled data, and to calibrate the multi-channel sampled data to implement impedance tomography imaging for the abnormal particle.

Optionally, the dynamic impedance imaging sensor may include a first annular electrical signal receiver, a second annular electrical signal receiver and an annular channel imaging sensor arranged in sequence according to direction of a fluid; each of the first annular electrical signal receiver, the second annular electrical signal receiver and the annular channel imaging sensor is provided with multiple electrodes; the first annular electrical signal receiver and the second annular electrical signal receiver are respectively connected to the impedance detection and flow rate measurement module through corresponding electrodes; and the annular channel imaging sensor is connected to the EIT instrument through the corresponding electrodes.

Optionally, the first annular electrical signal receiver may be provided thereon with two electrodes embedded in the tube wall; the second annular electrical signal receiver may be provided with two electrodes embedded in the tube wall; and the annular channel imaging sensor is provided with sixteen electrodes.

Optionally, the impedance detection and flow rate measurement module includes a first field-programmable gate array (FPGA) calculation and control module, an orthogonal excitation generation module, a first mixer, a second mixer, a first comparator and a second comparator;

- the orthogonal excitation generation module is respectively connected to the first FPGA calculation and control module, one electrode of the first annular electrical signal receiver, one electrode of the second annular electrical signal receiver, the first mixer and the second mixer; another electrode of the first annular electrical signal receiver is connected to the first mixer; another electrode of the second annular electrical signal receiver is connected to the second mixer; and the orthogonal excitation generation module is configured to generate a first orthogonal excitation signal and a second orthogonal excitation signal;
- the first annular electrical signal receiver is configured to receive the second orthogonal excitation signal, and output a voltage signal to the first mixer; and the second annular electrical signal receiver is configured to receive the second orthogonal excitation signal, and output a voltage signal to the second mixer;
- the first mixer and the second mixer are respectively connected to the first FPGA calculation and control module; the first mixer is configured to mix the first orthogonal excitation signal with the voltage signal output by the first annular electrical signal receiver to obtain a first mixing signal, and mix the second orthogonal excitation signal with the voltage signal output by the first annular electrical signal receiver to obtain a second mixing signal; the second mixer is configured to mix the first orthogonal excitation signal with the voltage signal output by the second annular electrical signal receiver to obtain a third mixing signal, and mix the second orthogonal excitation signal with the voltage signal output by the second annular electrical signal receiver to obtain a fourth mixing signal;
- the first FPGA calculation and control module is configured to calculate a first impedance amplitude information between the first annular electrical signal receiver and the second annular electrical signal receiver according to the first mixing signal and the second mixing signal, and calculate a second impedance amplitude information between the first annular electrical signal receiver and the second annular electrical signal receiver according to the third mixing signal and the fourth mixing signal;
- the first comparator is configured to generate a first pulse signal according to the first impedance amplitude information; the second comparator is configured to generate a second pulse signal according to the second impedance amplitude information; the first FPGA calculation and control module is further configured to calculate the flow rate of the abnormal particle according to the first pulse signal and the second pulse signal; and the second pulse signal is used as the synchronous trigger signal to trigger the EIT instrument.

Optionally, the impedance detection and flow rate measurement module may further include a first amplifier, a second amplifier, a third amplifier, a first current amplifier and a second current amplifier;

the orthogonal excitation generation module is connected to an input terminal of the first amplifier; an output terminal of the first amplifier is respectively connected to one electrode of the first annular electrical signal receiver and one electrode of the second annular electrical signal receiver; another electrode of the first annular electrical signal receiver is connected to the first mixer through the first current amplifier and the second amplifier in sequence; another electrode of the second annular electrical signal receiver is connected to the second mixer through the second current amplifier and the third amplifier in sequence.

Optionally, the impedance detection and flow rate measurement module further includes a first low-pass filter and a second low-pass filter;

the first low-pass filter is connected between the first mixer and the first FPGA calculation and control module; and the second low-pass filter is connected between the second mixer and the first FPGA calculation and control module.

Optionally, the impedance detection and flow rate measurement module may further include a first analog to digital converter (ADC), a second ADC, a third ADC, a fourth ADC, a first digital to analog converter (DAC) and a second DAC;

a first output terminal of the first low-pass filter is connected to the first FPGA calculation and control module through the first ADC, and a second output terminal of the first low-pass filter is connected to the first FPGA calculation and control module through the second ADC; a first output terminal of the second low-pass filter is connected to the first FPGA calculation and control module through the third ADC, and a second output terminal of the second low-pass filter is connected to the first FPGA calculation and control module through the fourth ADC; the first FPGA calculation and control module is connected to the first comparator through the first DAC; and the first FPGA calculation and control module is connected to the second comparator through the second DAC.

Optionally, the EIT instrument may include an analog switch array, a multi-channel interleaved sampling module, a second FPGA calculation and control module and an advanced reduced instruction set computer (RISC) machine (ARM) processor;

the second FPGA calculation and control module is respectively connected to the multi-channel interleaved sampling module, the analog switch array and the ARM processor; the analog switch array is connected to multiple electrodes of the annular channel imaging sensor; the analog switch array is connected to the multi-channel interleaved sampling module; the analog switch array is configured to inject a sinusoidal excitation current into the annular channel imaging sensor; the multi-channel interleaved sampling module is configured to, according to a principle of adjacent excitation and adjacent measurement, perform interleaved sampling on signals output by each electrode of the annular channel imaging sensor to acquire multi-channel sampled data; the second FPGA calculation and control module is configured to calibrate the multi-channel sampled data to acquire calibrated sampled data, and calculate voltage data from the calibrated sampled data; and the ARM processor is configured to implement impedance tomography imaging of the abnormal particle according to the voltage data.

Optionally, the second FPGA calculation and control module may include a narrow-band mode calibration module, a broad-band mode calibration module and an amplitude demodulation module;

the narrow-band mode calibration module is configured to calibrate the multi-channel sampled data to acquire calibrated sampled data when $$f_{in} < \frac{1}{8} f_s,$$

where $f_{in}$ is an input frequency of a measured single-dot-frequency signal, and $f_s$ is a sampling frequency of the multi-channel interleaved sampling module;

the broad-band mode calibration module is configured to calibrate the multi-channel sampled data to acquire calibrated sampled data when $$\frac{1}{8} f_s \le f_{in} < \frac{1}{4} f_s;$$

the amplitude demodulation module is configured to calculate voltage data from the calibrated sampled data.

Optionally, the narrow-band mode calibration module may include a finite impulse response (FIR) low-pass filter; the FIR low-pass filter is configured to perform low-pass filtering on the multi-channel sampled data;

the broad-band mode calibration module includes an orthogonal data generation unit, a fast Fourier transform (FFT) unit and a gain error and phase error calibration unit; the orthogonal data generation unit is configured to generate multiple of sets of orthogonal sequences; the FFT unit is configured to perform FFT for the multi-channel sampled data; and the gain error and phase error calibration unit is configured to eliminate a time phase error and a gain error of the sampled data after the FFT according to the orthogonal sequences.

Compared with the prior art, the beneficial effects of the present disclosure are summarized as follows.

The present disclosure proposes a dynamic impedance imaging system. In this system, the dynamic impedance imaging sensor can first determines whether there is an abnormal particle flowing through the tube. When there is an abnormal particle flowing through the tube, the impedance detection and flow rate measurement module successively sends out two hardware trigger signals to obtain the flow rate of the abnormal particle and generate a synchronous trigger signal. Under the trigger of the synchronous trigger signal, the EIT instrument injects a sinusoidal excitation current into the dynamic impedance imaging sensor, performs multi-channel interleaved sampling for the abnormal particle according to the flow rate to obtain multi-channel sampled data, and calibrates the multi-channel sampled data to implement impedance tomography imaging for the abnormal particle. The present disclosure is based on the multi-channel EIT instrument, and takes the impedance detection and flow rate measurement module as the guide to cooperate to complete the capture of the abnormal particle in the fluid. In addition, the present disclosure combines the interleaved sampling technology with the EIT technology to meet the requirements for bandwidth and the SNR in the fields of biomedicine and multiphase flow.

BRIEF DESCRIPTION OF THE DRAWINGS

In order to illustrate the technical solutions in the embodiments of the present disclosure or in the prior art more clearly, the accompanying drawings required in the embodiments are introduced below briefly. Apparently, the accompanying drawings in the following description show merely some embodiments of the present disclosure, and other drawings may be obtained from these accompanying drawings by those of ordinary skill in the art without creative labor.

DETAILED DESCRIPTION OF THE EMBODIMENTS

The technical solutions of the embodiments of the present disclosure are clearly and completely described below with reference to the accompanying drawings of the embodiments of the present disclosure. Apparently, the described embodiments are merely a part rather than all of the embodiments of the present disclosure. All other embodiments obtained by those of ordinary skill in the art based on the embodiments of the present disclosure without creative labor should fall within the protection scope of the present disclosure.

To make the above object, features and advantages of the present disclosure more obvious and easy to understand, the present disclosure is further described in detail below with reference to the accompanying drawings and specific implementations.

The dynamic impedance imaging system of the embodiments of the present disclosure provides, which is applied to dynamic imaging of cells, implement the capturing of an abnormal particle in a fluid by integrating (utilizing) the core technology of a microfluidic single-cell resistance detection system based on an EIT instrument. This embodiment combines the interleaved sampling technology with the EIT technology, such that the dynamic impedance imaging system can meet the requirements for bandwidth and SNR in the fields of biomedicine and multiphase flow.

Figure 1:
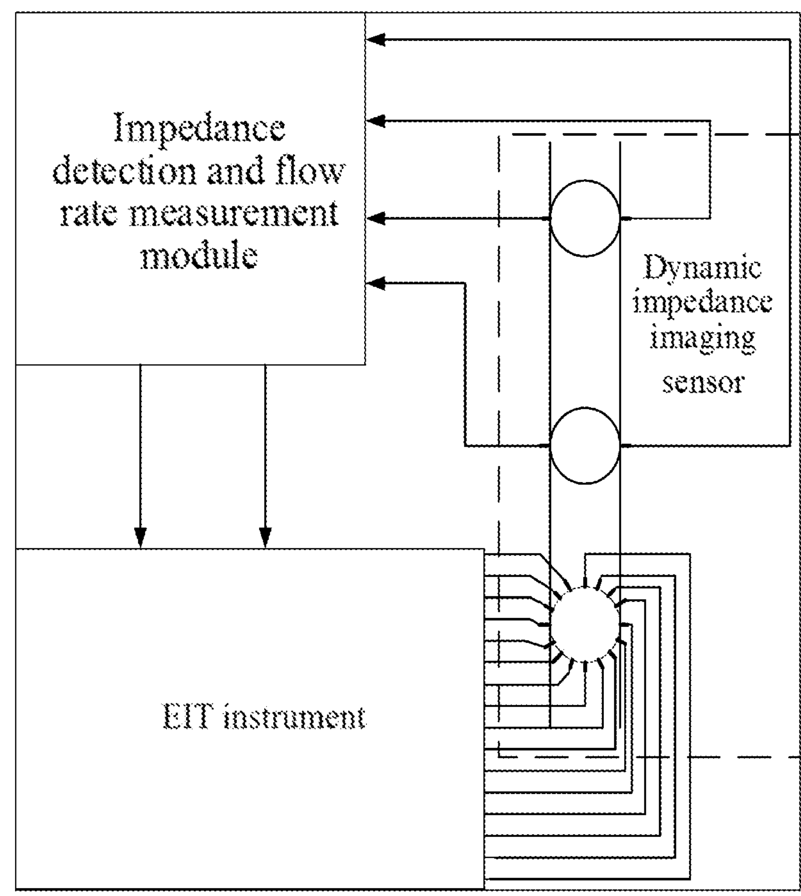
FIG. 1 is a structural schematic diagram of a dynamic impedance imaging system provided by an embodiment of the present disclosure.
Figure 2:
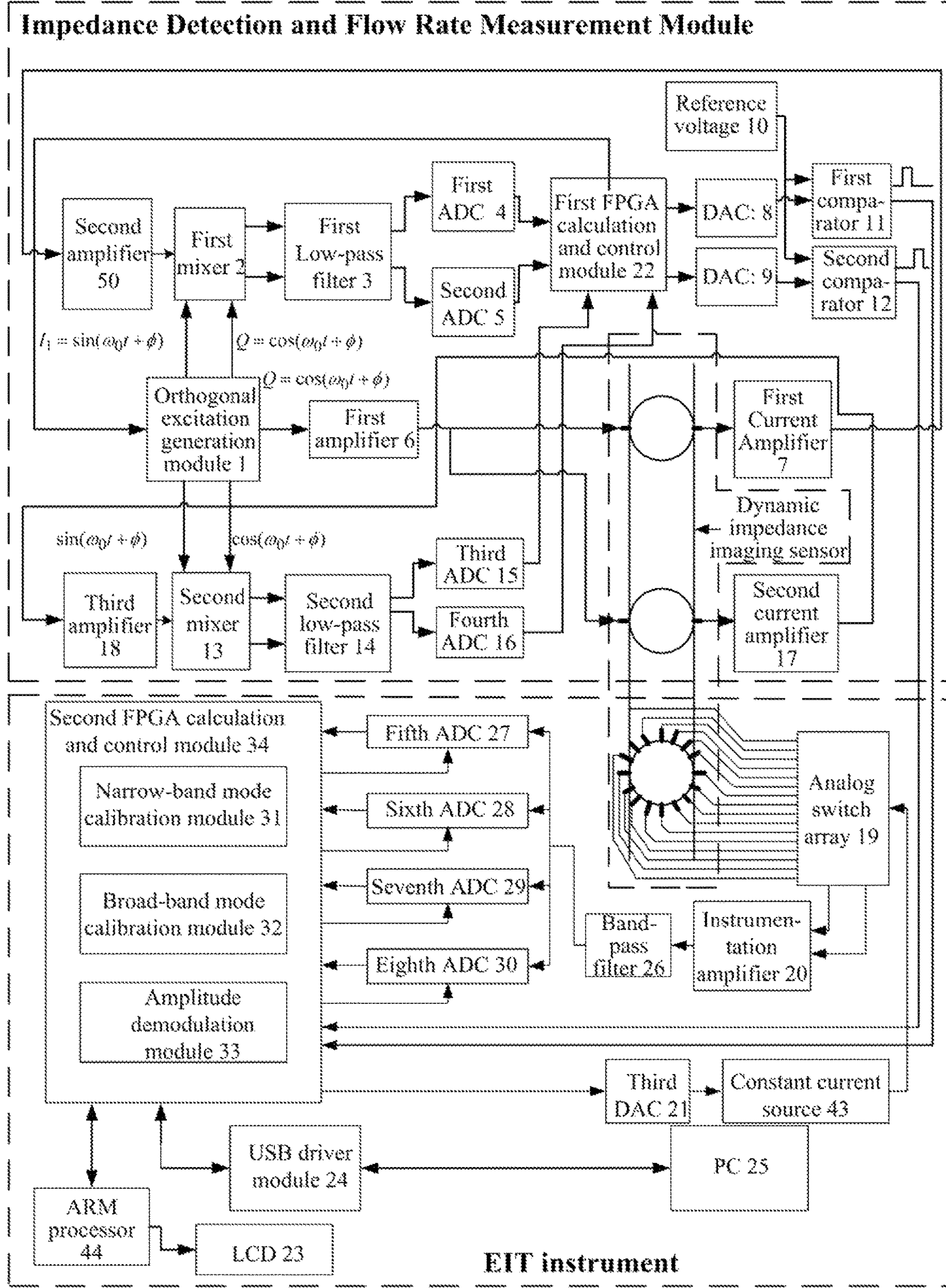
FIG. 2 is a structural block diagram of the dynamic impedance imaging system provided by an embodiment of the present disclosure.

FIG. 1 is a structural schematic diagram of the dynamic impedance imaging system provided by an embodiment of the present disclosure, and FIG. 2 is a structural block diagram of the dynamic impedance imaging system provided by an embodiment of the present disclosure. Referring to FIGS. 1 to 2, the dynamic impedance imaging system according to the present embodiment includes a dynamic impedance imaging sensor, an impedance detection and flow rate measurement module and the EIT instrument. The dynamic impedance imaging sensor is connected to the impedance detection and flow rate measurement module. The dynamic impedance imaging sensor is configured to determine whether there is an abnormal particle flowing through a tube. The impedance detection and flow rate measurement module is configured to detect the abnormal particle flowing through the dynamic impedance imaging sensor to obtain a flow rate of the abnormal particle, and generate a synchronous trigger signal to start the EIT instrument. The EIT instrument is respectively connected to the impedance detection and flow rate measurement module and the dynamic impedance imaging sensor. The EIT instrument is configured, in response to the triggering of the synchronous trigger signal, to inject a sinusoidal excitation current into the dynamic impedance imaging sensor, to perform multi-channel interleaved sampling for the abnormal particle according to the flow rate to acquire multi-channel sampled data, and to calibrate the multi-channel sampled data to implement impedance tomography imaging for the abnormal particle.

Figure 3:
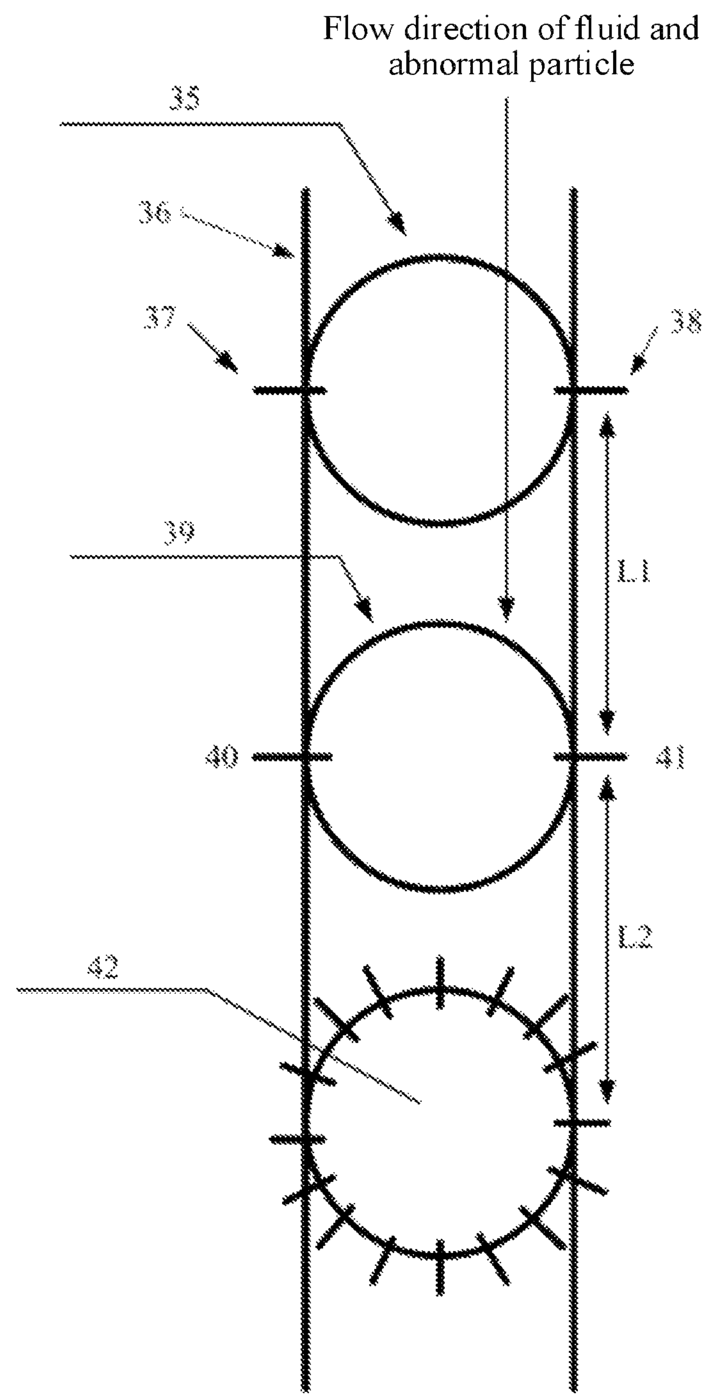
FIG. 3 is a structural block diagram of a dynamic impedance imaging sensor provided by an embodiment of the present disclosure.

FIG. 3 is a structural block diagram of the dynamic impedance imaging sensor provided by an embodiment of the present disclosure. Referring to FIG. 3, the dynamic impedance imaging sensor includes a first annular electrical signal receiver 35, a second annular electrical signal receiver and an annular channel imaging sensor 42 arranged in sequence according to flow direction of a fluid. The first annular electrical signal receiver 35, the second annular electrical signal receiver 39 and the annular channel imaging sensor 42 each are provided with multiple electrodes. The first annular electrical signal receiver 35 and the second annular electrical signal receiver are respectively connected to the impedance detection and flow rate measurement module through the corresponding electrodes. The annular channel imaging sensor 42 is connected to the EIT instrument through the corresponding electrodes.

As an optional implementation, the dynamic impedance imaging sensor includes a tube wall 36. The first annular electrical signal receiver 35 is provided with two electrodes embedded in the tube wall 36, which are an electrode 37 and an electrode 38 respectively. The second annular electrical signal receiver 39 is provided with two electrodes embedded in the tube wall 36, which are an electrode 40 and an electrode 41 respectively. The annular channel imaging sensor 42 is provided with sixteen electrodes, and the electrodes of the part of the annular channel imaging sensor 42 that contacts the tube wall 36 are embedded in the tube wall 36. The tube wall 36 is made of a transparent perspex material. The distance between the first annular electrical signal receiver 35 and the second annular electrical signal receiver 39 is $L_1$, and the distance between the second annular electrical signal receiver 39 and the annular channel imaging sensor 42 is $L_2$. The flow direction of the fluid and the abnormal particle is shown by an arrow in FIG. 3. When the abnormal particle flows through the first annular electrical signal receiver 35, the impedance detection and flow rate measurement module generates a first pulse signal $P_1$. Similarly, when the abnormal particle flows through the second annular electrical signal receiver 39, the impedance detection and flow rate measurement module generates a second pulse signal $P_2$. Provided that the distance $L_1$ between the first annular electrical signal receiver 35 and the second annular electrical signal receiver 39 is known, the flow rate of the abnormal particle can be obtained by acquiring a time difference $t_1$ between the first pulse signal $P_1$ and the second pulse signal $P_2$, namely, $v=L_1/t_1$. The second pulse signal $P_2$ is used as a start signal of the EIT instrument. When the EIT instrument detects the second pulse signal $P_2$, the EIT instrument starts to perform excitation and measurement imaging.

Figure 4:
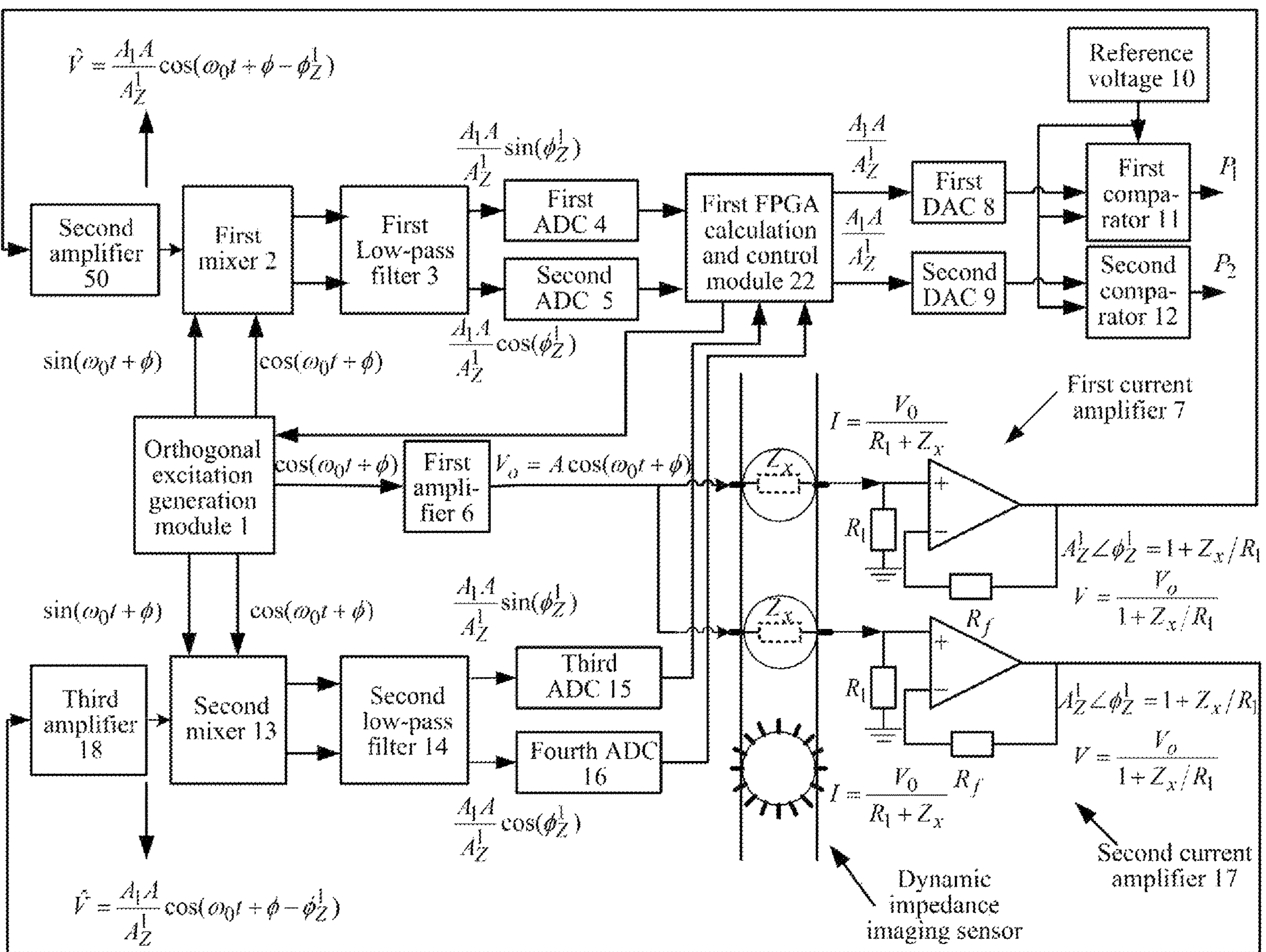
FIG. 4 is a structural block diagram of an impedance detection and flow rate measurement module provided by an embodiment of the present disclosure.

FIG. 4 is a structural block diagram of the impedance detection and flow rate measurement module provided by an embodiment of the present disclosure. Referring to FIG. 4, the impedance detection and flow rate measurement module includes a first FPGA calculation and control module 22, an orthogonal excitation generation module 1, a first mixer 2, a second mixer 13, a first comparator 11 and a second comparator 12. The first mixer 2 and the second mixer 13 are high precision mixers.

The orthogonal excitation generation module 1 is respectively connected to the first FPGA calculation and control module 22, one electrode of the first annular electrical signal receiver 35, one electrode of the second annular electrical signal receiver 39, the first mixer 2 and the second mixer 13. Another electrode of the first annular electrical signal receiver 35 is connected to the first mixer 2. Another electrode of the second annular electrical signal receiver 39 is connected to the second mixer 13. The orthogonal excitation generation module 1 is configured to generate a first orthogonal excitation signal and a second orthogonal excitation signal.

The first annular electrical signal receiver 35 is configured to receive the second orthogonal excitation signal, and output a voltage signal to the first mixer 2. The second annular electrical signal receiver 39 is configured to receive the second orthogonal excitation signal, and output a voltage signal to the second mixer 13.

The first mixer 2 and the second mixer 13 are respectively connected to the first FPGA calculation and control module 22. The first mixer 2 is configured to mix the first orthogonal excitation signal with the voltage signal output by the first annular electrical signal receiver 35 to obtain a first mixing signal, and mix the second orthogonal excitation signal with the voltage signal output by the first annular electrical signal receiver 35 to obtain a second mixing signal. The second mixer 13 is configured to mix the first orthogonal excitation signal with the voltage signal output by the second annular electrical signal receiver 39 to obtain a third mixing signal, and mix the second orthogonal excitation signal with the voltage signal output by the second annular electrical signal receiver 39 to obtain a fourth mixing signal.

The first FPGA calculation and control module 22 is configured to calculate a first impedance amplitude information between the first annular electrical signal receiver 35 and the second annular electrical signal receiver 39 according to the first mixing signal and the second mixing signal, and calculate a second impedance amplitude information between the first annular electrical signal receiver 35 and the second annular electrical signal receiver 39 according to the third mixing signal and the fourth mixing signal.

The first comparator 11 is configured to generate a first pulse signal according to the first impedance amplitude information. The second comparator 12 is configured to generate a second pulse signal according to the second impedance amplitude information. The first FPGA calculation and control module 22 is further configured to calculate the flow rate of the abnormal particle according to the first pulse signal and the second pulse signal. The second pulse signal is used as the synchronous trigger signal to trigger the EIT instrument.

As an optional implementation mode, the impedance detection and flow rate measurement module further includes a first amplifier 6, a second amplifier 50, a third amplifier 18, a first current amplifier 7 and a second current amplifier 17. The orthogonal excitation generation module 1 is connected to an input terminal of the first amplifier 6. An output terminal of the first amplifier 6 is respectively connected to one electrode of the first annular electrical signal receiver 35 and one electrode of the second annular electrical signal receiver 39. Another electrode on the first annular electrical signal receiver 35 is connected to the first mixer 2 through the first current amplifier 7 and the second amplifier 50 in sequence. Another electrode of the second annular electrical signal receiver 39 is connected to the second mixer 13 through the second current amplifier 17 and the third amplifier 18 in sequence.

As an optional implementation, the impedance detection and flow rate measurement module further includes a first low-pass filter 3 and a second low-pass filter 14. The first low-pass filter 3 is connected between the first mixer 2 and the first FPGA calculation and control module 22. The second low-pass filter 14 is connected between the second mixer 13 and the first FPGA calculation and control module 22.

As an optional implementation, the impedance detection and flow rate measurement module further includes a first analog to digital converter (ADC) 4, a second ADC 5, a third ADC 15, a fourth ADC 16, a first digital to analog converter (DAC) 8 and a second DAC 9. A first output terminal of the first low-pass filter 3 is connected to the first FPGA calculation and control module 22 through the first ADC 4, and a second output terminal of the first low-pass filter 3 is connected to the first FPGA calculation and control module 22 through the second ADC 5. A first output terminal of the second low-pass filter 14 is connected to the first FPGA calculation and control module 22 through the third ADC 15, and a second output terminal of the second low-pass filter 14 is connected to the first FPGA calculation and control module 22 through the fourth ADC 16. The first FPGA calculation and control module 22 is connected to the first comparator 11 through the first DAC 8. The first FPGA calculation and control module 22 is connected to the second comparator 12 through the second DAC 9.

As an optional implementation, the impedance detection and flow rate measurement module further includes a reference voltage 10, and the reference voltage 10 is connected to the first comparator 11 and the second comparator 12, respectively.

A specific implementation principle of the impedance detection and flow rate measurement module is as follows.

The orthogonal excitation generation module generates the first orthogonal excitation signal $I1=\sin(\omega_0 t+\varphi)$ and the second orthogonal excitation signal $Q=\cos(\omega_0 t+\varphi)$, where $\omega_0$ is an angular frequency of the excitation signal, $\varphi$ is a phase, and t is time. The second orthogonal excitation signal Q is input to the first amplifier 6, and is amplified by the first amplifier 6 to obtain a signal $V_0=A\cos(\omega_0 t+\varphi)$, where A is the amplitude of the signal. $V_0$ is applied to one electrode of the first annular electrical signal receiver 35 and one electrode of the second annular electrical signal receiver 39 as an excitation signal. Another electrode of the first annular electrical signal receiver 35 is connected to the first current amplifier 7, and another electrode of the second annular electrical signal receiver 39 is connected to the second current amplifier 17. Assuming that an impedance between the two electrodes of the first annular electrical signal receiver 35 and an impedance between the two electrodes of the second annular electrical signal receiver 39 are $Z_x$, then a current input to the first current amplifier 7 and the second current amplifier 17 is:

$$I = \frac{V_o}{R_1 + Z_x},$$

where $R_1$ is a resistance of a pull-down resistor.

An output voltage of the first current amplifier 7 and the second current amplifier 17 is:

$$V = \frac{Vo}{1 + Z_x / R_1};$$

where $1+Z_x/R_1=A_Z^1<\phi_Z^1$, $A_Z^1$ is an amplitude of $1+Z_x/R_1$ and $\phi_Z^1$ is a phase angle of $1+Z_x/R_1$. An output voltage generated by an output signal of the first current amplifier 7 through the second amplifier 50 and an output voltage generated by an output signal of the second current amplifier 17 through the third amplifier 18 are:

$$\hat{V} = \frac{A_1 A}{A_Z^1}\cos(\omega_0 t + \phi - \phi_Z^1);$$

where $A_1$ is a gain of the second amplifier 50 and the third amplifier 18. $\hat{V}$ is mixed with I1 and Q in the first mixer 2 and the second mixer 13. The first low-pass filter 3 and the second low-pass filter 14 perform low-pass filtering on a mixing result to output $$\frac{A_1 A}{A_Z^1}\sin(\phi_Z^1) \text{ and } \frac{A_1 A}{A_Z^1}\cos(\phi_Z^1)$$

respectively. The first ADC 4, the second ADC 5, the third ADC 15 and the fourth ADC 16 then sample output analog signals of the first low-pass filter 3 and the second low-pass filter 14, and send sampling results to the first FPGA calculation and control module 22 for calculation, so as to obtain the impedance amplitude information between the first annular electrical signal receiver 35 and the second annular electrical signal receiver 39:

$$Z = \frac{A_1 A}{A_Z^1}.$$

Meanwhile, the first FPGA calculation and control module 22 outputs the above impedance amplitude information in form of analog voltage through the first DAC 8 and the second DAC 9. If the impedance $Z_x$ between the first annular electrical signal receiver 35 and the second annular electrical signal receiver 39 does not change, the output of the first DAC 8 and the second DAC 9 is a direct current (DC) level. If there is an abnormal particle flowing through the first annular electrical signal receiver 35 and the second annular electrical signal receiver 39, the impedance $Z_x$ between the electrodes increases or decreases, and the above impedance amplitude information Z decreases or increases accordingly. When the abnormal particle flows through the first annular electrical signal receiver 35 and the second annular electrical signal receiver 39, the first DAC 8 and the second DAC 9 generate negative or positive pulses. The reference voltage 10, the first comparator 11 and the second comparator 12 shape the pulse signals generated by the first DAC 8 and the second DAC 9 into low-voltage complementary metal oxide semiconductor (LVCMOS) pulse signals $P_1$ and $P_2$. The first pulse signal $P_1$ is used as a timing start signal, and the second pulse signal $P_2$ is used as a timing end signal. By calculating the time interval $t_1$ between $P_1$ and $P_2$, the flow rate can be calculated when $L_1$ in FIG. 3 is known, that is, $v=L_1/t_1$. $L_1$ is the distance between the first annular electrical signal receiver 35 and the second annular electrical signal receiver 39. $P_2$ is also used as the synchronous trigger signal of the EIT instrument. When the second pulse signal $P_2$ arrives, the EIT instrument starts to operate.

Figure 5:
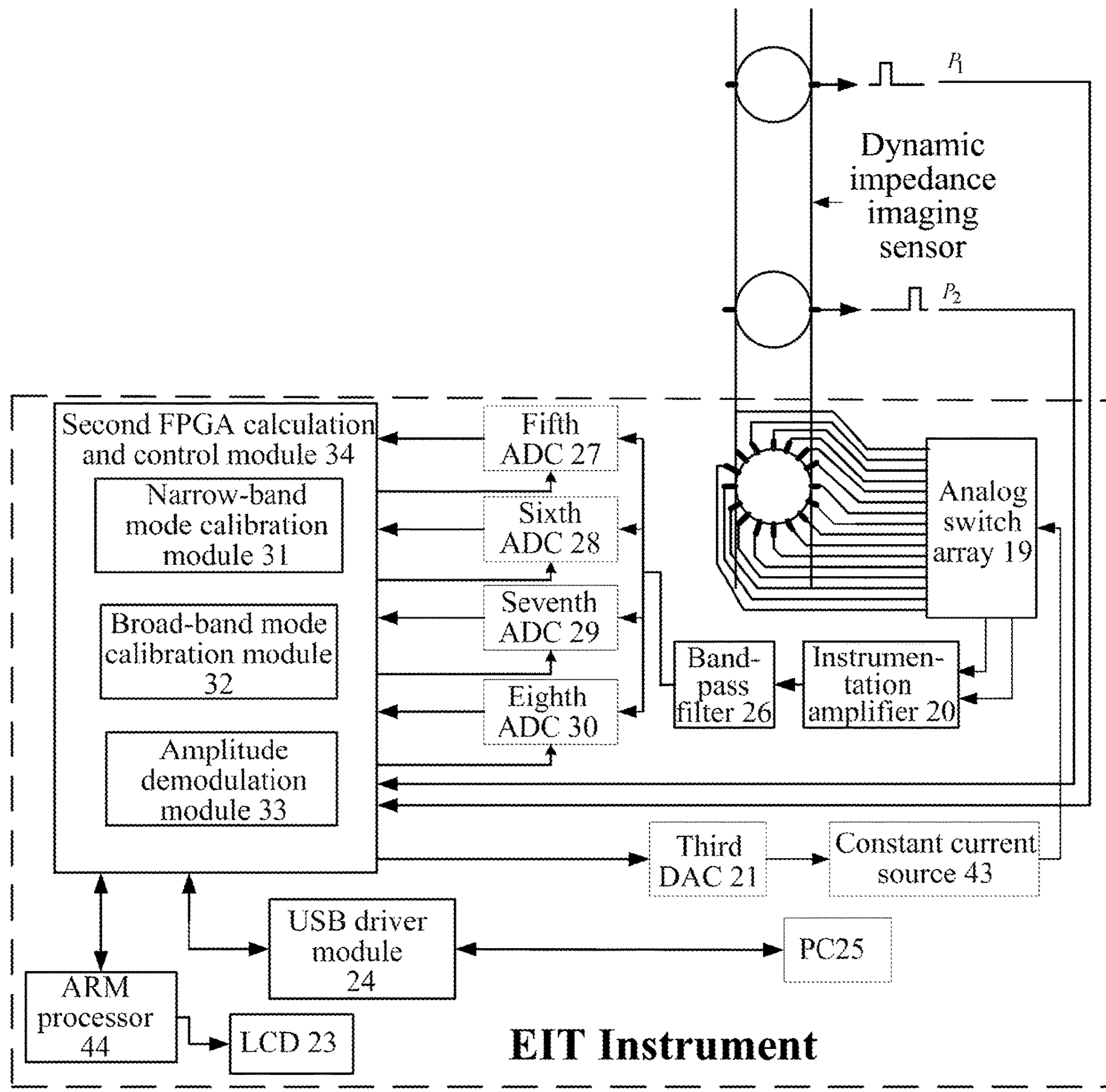
FIG. 5 is a structural block diagram of an electrical impedance tomographic (EIT) instrument provided by an embodiment of the present disclosure.

FIG. 5 is a structural block diagram of the EIT instrument provided by an embodiment of the present disclosure. Referring to FIG. 5, the EIT instrument includes an analog switch array 19, a multi-channel interleaved sampling module, a second FPGA calculation and control module 34 and an ARM processor 44. In this embodiment, the multi-channel interleaved sampling module is a four-channel interleaved sampling module, and the multi-channel interleaved sampling module includes a fifth ADC 27, a sixth ADC 28, a seventh ADC 29 and an eighth ADC 30. The fifth ADC 27, the sixth ADC 28, the seventh ADC 29 and the eighth ADC 30 are all 24-bit high-precision ADCs.

The second FPGA calculation and control module 34 is respectively connected to the multi-channel interleaved sampling module, the analog switch array 19 and the ARM processor 44. The analog switch array 19 is connected to the multiple electrodes of the annular channel imaging sensor 42. The analog switch array 19 is connected to the multi-channel interleaved sampling module. The analog switch array 19 is configured to inject a sinusoidal excitation current into the annular channel imaging sensor 42. The multi-channel interleaved sampling module is configured to, according to a principle of adjacent excitation and adjacent measurement, perform interleaved sampling on the signals output by each electrode of the annular channel imaging sensor 42 to acquire multi-channel sampled data. The second FPGA calculation and control module 34 is configured to calibrate the multi-channel sampled data to acquire calibrated sampled data, and calculate voltage data from the calibrated sampled data. The ARM processor 44 is configured to implement impedance tomography imaging of the abnormal particle according to the voltage data.

As an optional implementation, the EIT instrument further includes a third DAC 21, a constant current source 43, an instrumentation amplifier 20, a band-pass filter 26, a liquid crystal display (LCD) 23, a universal serial bus (USB) driver module 24 and a personal computer (PC) 25. A specific connection relationship of these components is shown in FIG. 5.

As an optional implementation, the second FPGA calculation and control module 34 includes a narrow-band mode calibration module 31, a broad-band mode calibration module 32 and an amplitude demodulation module 33. The narrow-band mode calibration module 31 is configured to calibrate the multi-channel sampled data to acquire calibrated sampled data when $$f_{in} < \frac{1}{8} f_s,$$

where $f_{in}$ is an input frequency of a measured single-dot-frequency signal, and $f_s$ is a sampling frequency of the multi-channel interleaved sampling module. The broad-band mode calibration module 32 is configured to calibrate the multi-channel sampled data to acquire calibrated sampled data when $$\frac{1}{8} f_s \le f_{in} < \frac{1}{4} f_s.$$

The amplitude demodulation module 33 is configured to calculate voltage data from the calibrated sampled data.

A specific implementation principle of the EIT instrument is as follows.

When the trigger signal $P_2$ arrives, the EIT instrument starts operating. The second FPGA calculation and control module 34 generates a sinusoidal excitation current through the third DAC 21 and the constant current source 43, and injects the sinusoidal excitation current into the annular channel imaging sensor through the analog switch array 19. According to a principle of adjacent excitation and adjacent measurement, when the sinusoidal excitation current is injected into electrodes m and m+1 (m<15) of the annular channel imaging sensor 42, the remaining electrodes perform synchronous measurement. The time consumed for each injection and synchronous measurement is $T_1$, and the time required to complete a frame of image is $T=13T_1$, the voltage data acquired by the synchronous measurement is $\tilde{V}$, and the voltage data $\tilde{V}$ is calculated by the amplitude demodulation module 33. The $L_2$ in FIG. 3 approximately satisfies the following relationship:

$$L_2 \approx T \times v.$$

In actual operation, $L_2$ is fixed in length after the processing of the annular channel imaging sensor 42 is completed, and the flow rate 1) is calculated by the flow rate calculation equation. Then the time for the system to generate each frame of image is calculated by the formula of the relationship approximately satisfied by the length of the above $L_2$, so as to obtain the time $T_1$ for each injection of excitation current and synchronous measurement.

where $$T_1 = \frac{L_2}{13v}.$$

A diameter of the annular channel imaging sensor 42 is D, and a three-dimensional (3D) sensitivity matrix is calculated for a cylindrical chamber with a length of $L_2$ and a diameter of D:

$$J(x,y,z) = -\int \nabla xyz(I^{ml}) \nabla xyz(I^n) dV, 1 \le x \le 64, 1 \le y \le 64, 1 \le z \le 16;$$

where J(x, y, z) is the 3D sensitivity matrix of the system, x is a number of points in an X-axis direction, Y is a number of points in a Y-axis direction, z is a number of points in a Z-axis direction, dV is a volume integral symbol, $\nabla xyz(I^{ml})$ is a gradient of a space potential for an m1-th excitation, and $\nabla xyz(I^n)$ is a gradient of a space potential for an n-th excitation. Then the above 3D sensitivity matrix is reduced to two-dimensional (2D) to obtain a 2D sensitivity matrix:

$$\tilde{J}(x, y) = \frac{\sum_{z=1}^{16} J(x, y, z)}{16}.$$

The above 2D sensitivity matrix and the measured voltage data $\tilde{V}$ are used to implement the tomography imaging for an object in an area of the annular channel imaging sensor 42:

$$\hat{\sigma} = \underset{\sigma}{\operatorname{argmin}} \frac{1}{2} \left\| \tilde{V} - \tilde{J}(x, y)\sigma \right\|;$$

where σ is a calculated intermediate variable, and σ becomes $\hat{\sigma}$ after a calculation iteration is completed. The second FPGA calculation and control module 34 sends the sampling data $\tilde{V}$ to the ARM processor 44. The ARM processor 44 completes the calculation of the tomography imaging, and displays the imaging result on the LCD. Alternatively, the acquired data may be sent to the PC 25 through the USB driver module 24 to complete calculation and graphic display.

In this embodiment, 4-channel interleaved sampling method is used to expand the sampling rate of the system while maintaining a high SNR. In actual use, a mismatch error caused by interleaved sampling needs to be calibrated. The narrow-band mode calibration module 31 and the broad-band mode calibration module 32 in the second FPGA calculation and control module are configured to calibrate the mismatch error of theinterleaved sampled data.

Figure 6:
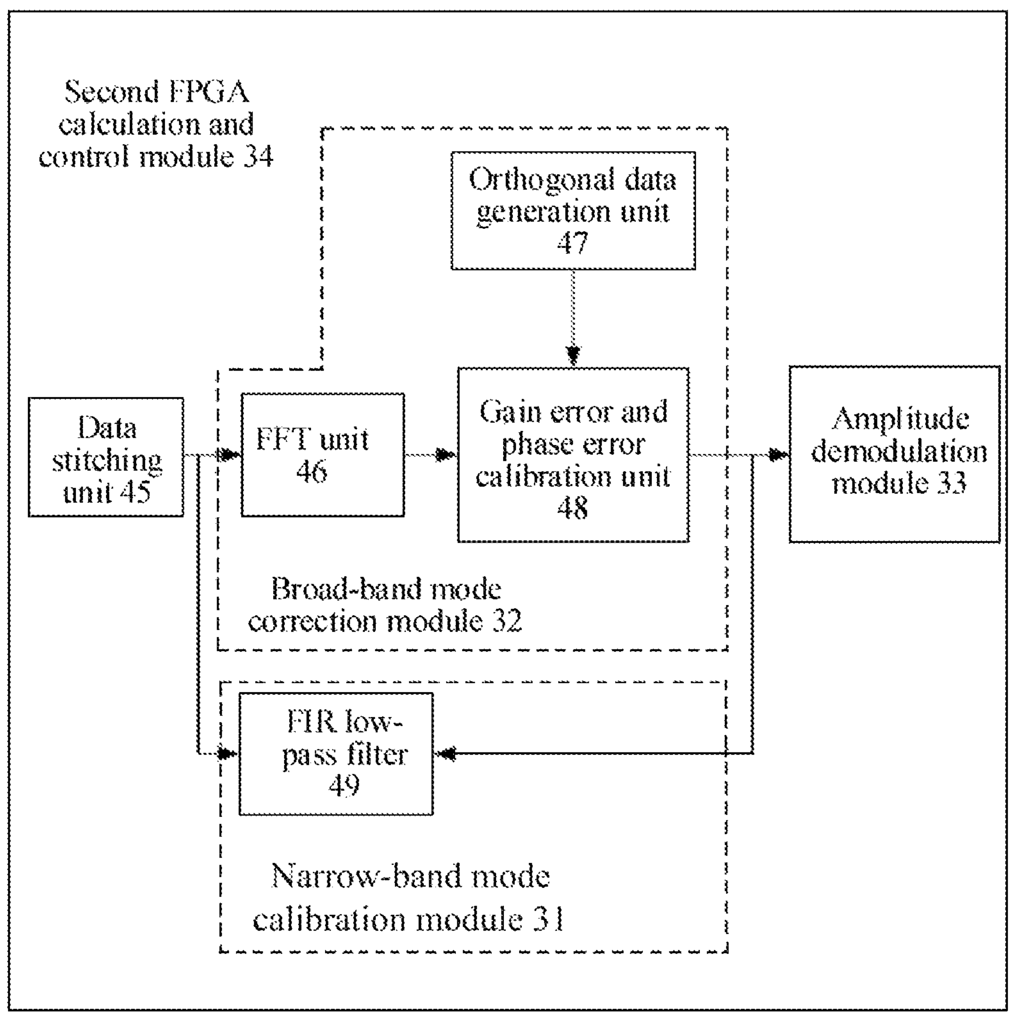
FIG. 6 is a structural block diagram of a second FPGA calculation and control module provided by an embodiment of the present disclosure.

FIG. 6 is a structural block diagram of the second FPGA calculation and control module 34 provided by an embodiment of the present disclosure. Referring to FIG. 6, the narrow-band mode calibration module 31 includes a finite impulse response (FIR) low-pass filter 49. The FIR low-pass filter 49 is configured to perform low-pass filtering on the multi-channel sampled data.

The broad-band mode calibration module 32 includes an orthogonal data generation unit 47, a fast Fourier transform (FFT) unit 46 and a gain error and phase error calibration unit 48. The orthogonal data generation unit 47 is configured to generate multiple sets of orthogonal sequences. The FFT unit 46 is configured to perform FFT for the multi-channel sampled data. The gain error and phase error calibration unit 48 is configured to eliminate a time phase error and a gain error of the sampled data after the FFT according to the orthogonal sequences.

A specific implementation principle of the second FPGA calculation and control module 34 is as follows.

A calibration algorithm part of the second FPGA calculation and control module 34 includes a data stitching unit 45, the FFT unit 46, the gain error and phase error calibration unit 48, the orthogonal data generation unit 47, the FIR low-pass filter 49 and the amplitude demodulation module 33.

For a four-channel interleaved sampling system, when the input frequency of the measured single-dot-frequency signal is $f_{in}$ and the system sampling rate is $f_s$, a noise spectrum caused by the time phase error and the gain error satisfies the following relationship:

$$\omega_n = \frac{k}{4}\omega_s \pm \omega_{in}, k = 1,2;$$

where $\omega_{in}=2\pi f_{in}$, $\omega_s=2\pi f_s$, and $\omega_n$ is an angular frequency of the noise spectrum.

If the four-channel interleaved sampled data is x[n] and the number of points is N, the sampled data x[n] is subjected to FFT to obtain x[k]. If a peak spectral point generated by the input signal is at a position of k, noise points generated by the mismatch error are at the following positions:

$$\begin{cases} k_2 = N/4 \pm k \\ k_3 = N/2 - k \end{cases};$$

where $k_2$ and $k_3$ are the positions of the noise points generated by the mismatch error. For a narrow-band operating mode, the frequency of the input signal is required to meet $f_{in}<1/8\,f_s$. After acquiring the four-channel interleaved sampled data, a low-pass filter $h_1[n]$ is configured to perform low-pass filtering to eliminate the noise spectrum caused by the time phase error and the gain error. $h_1[n]$ satisfies the following constraints:

$$\begin{cases} s_f \le \frac{1}{8} f_s \\ s_a \ge 40 \text{ dB} \end{cases};$$

where $s_f$ is a stopband cutoff frequency of $h_1[n]$, and $s_a$ is a stopband attenuation. The data after calibration in the narrow-band operating mode is $\tilde{x}[n]=x[n]*h_1[n]$, where * represents a convolution operation.

For a broad-band mode, the calibration algorithm calibrates as follows:

1. Given the four-channel interleaved sampled data x[n], performing FFT on the sampled data x[n] to obtain x[k], and calculating the position $k_1$ of the peak spectral point in the input signal, where the number of points is N.
2. Calculating positions of the noise points generated by the mismatch error $$\begin{cases} k_2 = N/4 \pm k_1 \\ k_3 = N/2 - k_1 \end{cases}.$$

3. Calculating noise frequencies according to the above positions of the noise points $$\begin{cases} f_{k_1} = \frac{f_s}{N}\left(\frac{N}{4} + k_1\right) \\ f_{k_2} = \frac{f_s}{N}\left(\frac{N}{4} - k_1\right), \\ f_{k_3} = \frac{f_s}{N}\left(\frac{N}{2} - k_1\right) \end{cases}$$

where $f_{k_1}$, $f_{k_2}$, and $f_{k_3}$ are values of noise frequencies estimated according to the positions $k_2$ and $k_3$ of the noise points, respectively.

4. Generating three sets of standard orthogonal sequences based on the above noise frequencies $$\begin{cases} Q_1[n] = \cos(2\pi f_{k_1} \frac{1}{f_s} n) \\ I_1[n] = \sin(2\pi f_{k_1} \frac{1}{f_s} n) \\ Q_2[n] = \cos(2\pi f_{k_2} \frac{1}{f_s} n) \\ I_2[n] = \sin(2\pi f_{k_2} \frac{1}{f_s} n) \\ Q_3[n] = \cos(2\pi f_{k_3} \frac{1}{f_s} n) \\ I_3[n] = \sin(2\pi f_{k_3} \frac{1}{f_s} n) \end{cases}.$$

where $Q_1[n]$ and $I_1[n]$ are a set of standard orthogonal sequences generated according to the noise frequency $f_{k_1}$ in Step 3; $Q_2[n]$ and $I_2[n]$ are a set of standard orthogonal sequences generated according to the noise frequency $f_{k_2}$ in Step 3; $Q_3[n]$ and $I_3[n]$ are a set of standard orthogonal sequences generated according to the noise frequency $f_{k_3}$ in Step 3. In this embodiment, the orthogonal sequences $Q_3,I_3,Q_2,I_2,Q_1,I_1$ are generated by a coordinate rotation digital computer (CORDIC) algorithm, but the method for generation of the orthogonal sequences is not limited thereto. The combination of the CORDIC algorithm and the algorithm in this embodiment avoids the use of a memory during the generation of the orthogonal sequences, thereby saving storage space and saving time in the process of reading the internal storage. The following describes the combination of the CORDIC algorithm and the algorithm of this embodiment to generate the orthogonal sequences $Q_3,I_3,Q_2,I_2,Q_1,I_1$.

5. Generating phase stepping $$\begin{cases} \theta_{f_{k_1}} = \frac{2\pi(N+4k_1)}{4N} \\ \theta_{f_{k_2}} = \frac{2\pi(N-4k_1)}{4N} \\ \theta_{f_{k_3}} = \frac{2\pi(N-2k_1)}{2N} \end{cases}.$$

where $\theta_{f_{k1}}$ is a phase stepping for generating the orthogonal sequences $Q_1[n]$ and $I_1[n]$; $\theta_{f_{k2}}$ is a phase stepping for generating the orthogonal sequences $Q_2[n]$ and $I_2[n]$; and $\theta_{f_{k3}}$ is a phase stepping for generating the orthogonal sequences $Q_3[n]$ and $I_3[n]$.

6. Generating CORDIC initial values $$\begin{cases} x_0^{k_i} = k = 0.607263 \\ y_0^{k_i} = 0 \\ z_0^{k_i} = 0 \end{cases}, i \in [1,3]$$

where the use of CORDIC algorithm to generate the orthogonal sequences $Q_1[n]$, $I_1[n]$, $Q_2[n]$, $I_2[n]$, $Q_3[n]$ and $I_3[n]$ requires initial values, which are $x_0^{k_1}$, $y_0^{k_1}$, $z_0^{k_1}$, $x_0^{k_2}$, $y_0^{k_2}$, $z_0^{k_2}$ and $x_0^{k_3}$, $y_0^{k_3}$, $z_0^{k_3}$ respectively. The superscript $k_i$ is used here to distinguish the three different sets of initial values, and i ranges from 1 to 3.

7. Performing iterative calculations $$\begin{cases} S_m^{k_i} = \begin{cases} -1, Z_m^{k_i} < 0 \\ +1, Z_m^{k_i} \ge 0 \end{cases} \\ x_{m+1}^{k_i} = x_m^{k_i} - S_m^{k_i} 2^{-m} y_m^{k_i} \\ y_{m+1}^{k_i} = y_m^{k_i} + S_m^{k_i} 2^{-m} x_m^{k_i} \\ z_{m+1}^{k_i} = z_m^{k_i} - S_m^{k_i} \arctan(2^{-m}) \end{cases} \quad i \in [1,3],\ m \in [1,15]$$

where iterative calculations are performed through the CORDIC algorithm, and a desired precision is achieved after 15 iterations. $x_m^{k_i}$ and $y_m^{k_i}$ are final iteration values, and $s_m^{k_i}$ and $Z_m^{k_i}$ are intermediate variables of the iteration. The three sets of orthogonal sequences require three sets of iterations. The subscript 1 is used to distinguish the different orthogonal sequences, and i ranges from 1 to 3.

8. Calculating the orthogonal sequences $$\begin{cases} Q_i[1] = x_{16}^{k_i} \\ I_i[1] = y_{16}^{k_i} \end{cases}, i \in [1,3].$$

where $Q_i^1$ and $I_i^1$ and represent the three sets of orthogonal sequences, which are distinguished by the subscript 1, for i∈[1,3]. $x_{16}^{k_i}$ and $y_{16}^{k_i}$ are calculation results obtained in the previous step.

19. Updating the CORDIC initial values $$\begin{cases} x_0^{k_i} = k = 0.607263 \\ y_0^{k_i} = 0 \\ z_0^{k_i} = n\theta_{f_{k_i}}, n \in [2, N] \end{cases}, i \in [1,3].$$

10. Repeating Steps 4, 5 and 6

$$\begin{cases} Q_i[n] = x_{16}^{k_i} \\ I_i[n] = y_{16}^{k_i} \end{cases}, n \in [2,N], i \in [1,3].$$

11. Calculating cross-correlation $$\begin{cases} R_{xQ_k} = \frac{1}{N_0}\sum_{n=1}^{N_0} x[n]Q_k[n] \\ R_{xI_k} = \frac{1}{N_0}\sum_{n=1}^{N_0} x[n]I_k[n] \end{cases}, k \in [1,2,3], N_0 \ll N$$

where $N_0$ is a number of cross-correlation calculation points, and $R_{xQ_k}$ and $R_{xI_k}$ are cross-correlation calculation results between the sampled data x[n] and $Q_k$[n], $I_k$[n].

12. Obtaining phase and amplitude information of the noise spectrum $$\theta_k = \begin{cases} \arctan\left|\frac{R_{xQ_k}}{R_{xI_k}}\right|, R_{xQ_k} > 0, R_{xI_k} > 0 \\ -\arctan\left|\frac{R_{xQ_k}}{R_{xI_k}}\right|, R_{xQ_k} < 0, R_{xI_k} > 0 \\ \arctan\left|\frac{R_{xQ_k}}{R_{xI_k}}\right| + \pi, R_{xQ_k} < 0, R_{xI_k} < 0 \\ \pi - \arctan\left|\frac{R_{xQ_k}}{R_{xI_k}}\right|, R_{xQ_k} > 0, R_{xI_k} < 0 \end{cases}, k \in [1,2,3],$$

$$A_k = 2\sqrt{R_{xQ_k}^2 + R_{xI_k}^2}, k = [1,2,3]$$

where $\theta_k$ is obtained phase information, and $A_k$ is obtained amplitude information, for k∈[1,3].

13. Reconstructing four-channel interleaved sampled mismatch error data e[n] according to the calculated amplitude and phase information.

$$e[n] = A_1\cos(2\pi f_{k_1}\frac{n}{f_s} + \theta_1) + A_2\cos(2\pi f_{k_2}\frac{n}{f_s} + \theta_2) + A_3\cos(2\pi f_{k_3}\frac{n}{f_s} + \theta_3),$$

where $A_1$, $A_2$ and $A_3$ are the amplitude information $A_k$ in Step 11, for k∈[1, 2,3]; and $\theta_1$, $\theta_2$ and $\theta_3$ are the phase information in Step 11.

14. Completing the calibration of the four-channel interleaved sampled data by subtracting the mismatch error e[n] from the acquired data x[n] and then acquiring calibrated data $$\tilde{x}[n]=x[n]-e[n].$$

In order to obtain a more accurate amplitude demodulation value, the frequency of the input signal in the broadband mode is $$f_{in} < \frac{1}{4}f_s.$$

The amplitude demodulation module demodulates the amplitude information of the sampling signal by calculating an average value.

The advantages of the dynamic impedance imaging system in this embodiment are as follows. The dynamic impedance imaging system can capture the abnormal particle flowing in the dynamic impedance imaging sensor, measure the flow rate of the abnormal particle, and perform electrical impedance tomography imaging on the abnormal particle after obtaining the flow rate of the abnormal particle.

In particular, the dynamic impedance imaging sensor first determines whether there is an abnormal particle flowing through the tube, and sends out two hardware trigger signals $P_1$ and $P_2$ successively when there is an abnormal particle flowing through the sensor. The $P_1$ and $P_2$ are used as gate signals for the hardware system to obtain the flow rate ν of the abnormal particle (usually a cell cluster). The gate signal $P_2$ and the flow rate ν are used as start and scan time control signals to start and control the EIT system.

The impedance detection and flow rate measurement module may detect an impedance change between the two measurement electrodes when the fluid passes through the dynamic impedance imaging sensor. It converts this change into a standard LVCMOS level output to measure the flow rate of the abnormal particle in the fluid and provide a start signal for the EIT instrument.

The dynamic impedance imaging system is based on a 16-channel EIT instrument, and has the impedance detection and flow rate measurement module in the leading position. These two systems cooperate to complete the capture of the abnormal particle in the fluid.

This embodiment proposes a calibration algorithm of an interleaved sampled mismatch error suitable for the dynamic impedance imaging system. The calibration algorithm can be embodied in two operating modes, broad-band and narrow-band, and the two different operating modes can be selected according to actual operating conditions so as to achieve a balance between performance and resources.

This embodiment combines the interleaved sampling technology and the EIT technology to satisfy the requirements for the SNR and sampling rate (bandwidth) of the EIT system in the biomedical field.

Each embodiment of the present specification is described in a progressive manner, each embodiment focuses on the difference from other embodiments, and the same and similar parts between the embodiments may refer to each other.

In this specification, several embodiments are used for illustration of the principles and implementations of the present disclosure. The description of the above embodiments is used to help understand the method of the present disclosure and the core idea thereof. In addition, those of ordinary skill in the art can make various modifications in terms of specific implementations and scope of application in accordance with the teachings of the present disclosure. In conclusion, the content of the present specification shall not be construed as a limitation to the present disclosure.

What is claimed is:

1. A dynamic impedance imaging system, comprising a dynamic impedance imaging sensor, an impedance detection and flow rate measurement module and an electrical impedance tomographic (EIT) instrument, wherein the dynamic impedance imaging sensor is connected to the impedance detection and flow rate measurement module; the dynamic impedance imaging sensor is configured to determine whether there is an abnormal particle flowing through a tube; the dynamic impedance imaging sensor comprises a first annular electrical signal receiver, a second annular electrical signal receiver and an annular channel imaging sensor arranged in sequence according to direction of a fluid; each of the first annular electrical signal receiver, the second annular electrical signal receiver and the annular channel imaging sensor is provided with a plurality of electrodes; the first annular electrical signal receiver and the second annular electrical signal receiver are respectively connected to the impedance detection and flow rate measurement module through corresponding electrodes; and the annular channel imaging sensor is connected to the EIT instrument through the corresponding electrodes;

the impedance detection and flow rate measurement module is configured to detect the abnormal particle flowing through the dynamic impedance imaging sensor to obtain a flow rate of the abnormal particle, and generate a synchronous trigger signal;

the EIT instrument is respectively connected to the impedance detection and flow rate measurement module and the dynamic impedance imaging sensor; the EIT instrument is configured to inject a sinusoidal excitation current into the dynamic impedance imaging sensor under triggering of the synchronous trigger signal, to perform multi-channel interleaved sampling for the abnormal particle according to the flow rate to acquire multi-channel sampled data, and to calibrate the multi-channel sampled data to implement impedance tomography imaging for the abnormal particle; the EIT instrument comprises an analog switch array, a multi-channel interleaved sampling module, a second FPGA calculation and control module and an advanced reduced instruction set computer (RISC) machine (ARM) processor;

the second FPGA calculation and control module is respectively connected to the multi-channel interleaved sampling module, the analog switch array and the ARM processor; the analog switch array is connected to the plurality of electrodes of the annular channel imaging sensor; the analog switch array is connected to the multi-channel interleaved sampling module; the analog switch array is configured to inject a sinusoidal excitation current into the annular channel imaging sensor; the multi-channel interleaved sampling module is configured to, according to a principle of adjacent excitation and adjacent measurement, perform interleaved sampling on signals output by each electrode of the annular channel imaging sensor to acquire multi-channel sampled data; the second FPGA calculation and control module is configured to calibrate the multi-channel sampled data to acquire calibrated sampled data, and calculate voltage data from the calibrated sampled data; and the ARM processor is configured to implement impedance tomography imaging of the abnormal particle according to the voltage data;

the second FPGA calculation and control module comprises a narrow-band mode calibration module, a broad-band mode calibration module and an amplitude demodulation module;

the narrow-band mode calibration module is configured to calibrate the multi-channel sampled data to acquire calibrated sampled data when $f_{in}<\frac{1}{8} f_s$, where $f_{in}$ is an input frequency of a measured single-dot-frequency signal, and $f_s$ is a sampling frequency of the multi-channel interleaved sampling module;

the broad-band mode calibration module is configured to calibrate the multi-channel sampled data to acquire calibrated sampled data when $\frac{1}{8} f_s \leq f_{in} \leq \frac{1}{4} f_s$; and the amplitude demodulation module is configured to calculate voltage data from the calibrated sampled data.

2. The dynamic impedance imaging system according to claim 1, wherein the first annular electrical signal receiver is provided with two electrodes embedded in the tube wall; the second annular electrical signal receiver is provided with two electrodes embedded in the tube wall; and the annular channel imaging sensor is provided with sixteen electrodes.

3. The dynamic impedance imaging system according to claim 1, wherein the impedance detection and flow rate measurement module comprises a first field-programmable gate array (FPGA) calculation and control module, an orthogonal excitation generation module, a first mixer, a second mixer, a first comparator and a second comparator;

the orthogonal excitation generation module is respectively connected to the first FPGA calculation and control module, one electrode of the first annular electrical signal receiver, one electrode of the second annular electrical signal receiver, the first mixer and the second mixer; another electrode of the first annular electrical signal receiver is connected to the first mixer; another electrode of the second annular electrical signal receiver is connected to the second mixer; and the orthogonal excitation generation module is configured to generate a first orthogonal excitation signal and a second orthogonal excitation signal;

the first annular electrical signal receiver is configured to receive the second orthogonal excitation signal, and output a voltage signal to the first mixer; and the second annular electrical signal receiver is configured to receive the second orthogonal excitation signal, and output a voltage signal to the second mixer;

the first mixer and the second mixer are respectively connected to the first FPGA calculation and control module; the first mixer is configured to mix the first orthogonal excitation signal with the voltage signal output by the first annular electrical signal receiver to obtain a first mixing signal, and mix the second orthogonal excitation signal with the voltage signal output by the first annular electrical signal receiver to obtain a second mixing signal; the second mixer is configured to mix the first orthogonal excitation signal with the voltage signal output by the second annular electrical signal receiver to obtain a third mixing signal, and mix the second orthogonal excitation signal with the voltage signal output by the second annular electrical signal receiver to obtain a fourth mixing signal;

the first FPGA calculation and control module is configured to calculate a first impedance amplitude information between the first annular electrical signal receiver and the second annular electrical signal receiver according to the first mixing signal and the second mixing signal, and calculate a second impedance amplitude information between the first annular electrical signal receiver and the second annular electrical signal receiver according to the third mixing signal and the fourth mixing signal;

the first comparator is configured to generate a first pulse signal according to the first impedance amplitude information; the second comparator is configured to generate a second pulse signal according to the second impedance amplitude information; the first FPGA calculation and control module is further configured to calculate the flow rate of the abnormal particle according to the first pulse signal and the second pulse signal; and the second pulse signal is used as the synchronous trigger signal to trigger the EIT instrument.

4. The dynamic impedance imaging system according to claim 3, wherein the impedance detection and flow rate measurement module further comprises a first amplifier, a second amplifier, a third amplifier, a first current amplifier and a second current amplifier;

the orthogonal excitation generation module is connected to an input terminal of the first amplifier; an output terminal of the first amplifier is respectively connected to one electrode of the first annular electrical signal receiver and one electrode of the second annular electrical signal receiver; another electrode of the first annular electrical signal receiver is connected to the first mixer through the first current amplifier and the second amplifier in sequence; another electrode of the second annular electrical signal receiver is connected to the second mixer through the second current amplifier and the third amplifier in sequence.

5. The dynamic impedance imaging system according to claim 4, wherein the impedance detection and flow rate measurement module further comprises a first low-pass filter and a second low-pass filter;

the first low-pass filter is connected between the first mixer and the first FPGA calculation and control module; and the second low-pass filter is connected between the second mixer and the first FPGA calculation and control module.

6. The dynamic impedance imaging system according to claim 5, wherein the impedance detection and flow rate measurement module further comprises a first analog to digital converter (ADC), a second ADC, a third ADC, a fourth ADC, a first digital to analog converter (DAC) and a second DAC;

a first output terminal of the first low-pass filter is connected to the first FPGA calculation and control module through the first ADC, and a second output terminal of the first low-pass filter is connected to the first FPGA calculation and control module through the second ADC; a first output terminal of the second low-pass filter is connected to the first FPGA calculation and control module through the third ADC, and a second output terminal of the second low-pass filter is connected to the first FPGA calculation and control module through the fourth ADC; the first FPGA calculation and control module is connected to the first comparator through the first DAC; and the first FPGA calculation and control module is connected to the second comparator through the second DAC.

7. The dynamic impedance imaging system according to claim 1, wherein the narrow-band mode calibration module comprises a finite impulse response (FIR) low-pass filter; the FIR low-pass filter is configured to perform low-pass filtering on the multi-channel sampled data;

the broad-band mode calibration module comprises an orthogonal data generation unit, a fast Fourier transform (FFT) unit and a gain error and phase error calibration unit; the orthogonal data generation unit is configured to generate a plurality of sets of orthogonal sequences; the FFT unit is configured to perform FFT for the multi-channel sampled data; and the gain error and phase error calibration unit is configured to eliminate a time phase error and a gain error of the sampled data after the FFT according to the orthogonal sequences.

* * * * *